United States Patent [19]

Moinet et al.

[11] Patent Number: 4,647,557

[45] Date of Patent: Mar. 3, 1987

[54] NOVEL HETEROCYCLIC DERIVATIVES BEARING AN AMINO RADICAL, PROCESSES FOR THEIR PRODUCTION AND THE PHARMACEUTICAL COMPOSITIONS CONTAINING THEM

[76] Inventors: Gérard Moinet, 15, Rue Lamartine, 91400 Orsay; Michel Schaeffer, 4, Rue François Girardon; Pierre Bessin, Allée Bossuet, both of 91380 Chilly Mazarin; Jacqueline Bonnet, 19, Rue Charcot, 75013 Paris, all of France

[21] Appl. No.: 564,918

[22] Filed: Dec. 23, 1983

[30] Foreign Application Priority Data

Dec. 28, 1982 [CH] Switzerland .................. 7591/82

[51] Int. Cl.$^4$ ............... A01N 43/50; A01N 43/78; C07D 233/16; C07D 233/44

[52] U.S. Cl. .................. 514/210; 544/54; 540/544; 544/55; 544/58.7; 540/553; 544/58.5; 544/63; 514/212; 544/72; 544/96; 514/222; 544/98; 544/128; 514/226; 544/133; 544/139; 514/227; 544/333; 544/374; 514/228; 544/363; 544/369; 514/230; 544/370; 546/153; 514/234; 546/155; 546/156; 514/236; 546/171; 546/172; 514/237; 546/174; 546/176; 514/239; 546/177; 546/197; 514/240; 546/200; 546/203; 514/255; 546/204; 546/205; 514/312; 546/206; 546/278; 514/313; 548/181; 548/190; 514/314; 548/193; 548/194; 514/317; 548/195; 548/196; 514/319; 548/197; 548/198; 514/321; 548/309; 548/315; 514/322; 548/327; 548/336; 514/325; 548/337; 548/342; 514/326; 548/343; 548/348; 514/333; 548/351; 548/374; 514/341; 514/342; 514/370; 514/397; 514/398; 514/401; 514/402; 544/3

[58] Field of Search ............... 548/309, 315, 337, 181, 548/196, 194, 193, 190, 195, 197, 198, 336, 342, 343, 348, 351, 324, 374; 544/54, 55, 63, 72, 96, 98, 128, 133, 139, 333, 58.7, 58.5, 374, 363, 369, 370, 3; 546/256, 270, 273, 280, 171, 172, 174, 176, 177, 153, 155, 156, 203, 204, 205, 206, 197, 199, 200, 278; 260/239 A, 245.5; 514/210, 212, 222, 226, 227, 228, 230, 234, 236, 237, 239, 240, 255, 312, 313, 314, 317, 319, 321, 322, 325, 326, 333, 341, 342, 370, 397, 398, 401, 402

[56] References Cited

U.S. PATENT DOCUMENTS

| | | | |
|---|---|---|---|
| 2,331,995 | 10/1943 | Mathes | 548/190 |
| 2,636,037 | 4/1953 | Sprague | 548/195 |
| 3,489,757 | 1/1970 | Koppe | 548/193 |
| 3,804,833 | 4/1974 | Stänle | 548/337 |
| 3,926,982 | 12/1975 | Rovnyak | 544/55 |
| 3,927,014 | 12/1975 | Rovnyak | 544/55 |
| 4,058,616 | 11/1977 | Kummer | 548/315 |
| 4,152,329 | 5/1979 | Cahoy | 548/195 |
| 4,165,377 | 8/1979 | Jones | 548/337 |
| 4,165,378 | 8/1979 | Gilman | 548/337 |
| 4,269,978 | 5/1981 | Petitpierre | 548/190 |
| 4,347,370 | 8/1982 | Gilman | 548/337 |
| 4,374,143 | 2/1983 | Dolman | 548/315 |
| 4,501,750 | 2/1985 | Sakano | 548/195 |
| 4,560,751 | 12/1985 | Seybold | 548/190 |

*Primary Examiner*—C. Warren Ivy
*Attorney, Agent, or Firm*—Omri M. Behr

[57] ABSTRACT

This invention relates to novel heterocyclic derivatives bearing an amino group and to processes for making said compounds.

More particularly this invention provides novel heterocyclic compounds the hetero ring of which has two hetero atoms, the same or different, substituted with a free or substituted amino group.

These compounds are useful as active ingredients of drugs.

12 Claims, No Drawings

NOVEL HETEROCYCLIC DERIVATIVES BEARING AN AMINO RADICAL, PROCESSES FOR THEIR PRODUCTION AND THE PHARMACEUTICAL COMPOSITIONS CONTAINING THEM

SUMMARY OF THE INVENTION

This invention provides novel compounds having the formula I

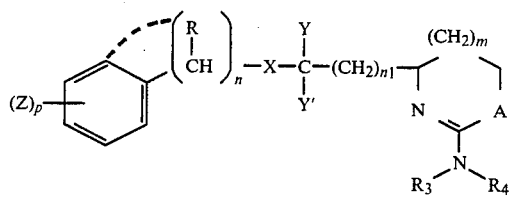

and the acid addition salts thereof with a mineral or organic acid, preferably a therapeutically-compatible acid. This invention also provide processes for producing compounds of formula I starting from an alkylenylated derivative from an oxiranyl derivative.

These compounds find an use in human therapy as active ingredients of pharmaceutical compositions intended to alleviate cardio-vascular failure or to counteract depressive conditions.

This invention relates to novel heterocyclic derivatives bearing an amino group and to process for making said compounds.

More particularly this invention provides novel heterocyclic compounds the hetero ring of which has two heteroatoms the same or different, substituted with a free or substituted amino group.

Specifically this invention provides the compounds having the formula I

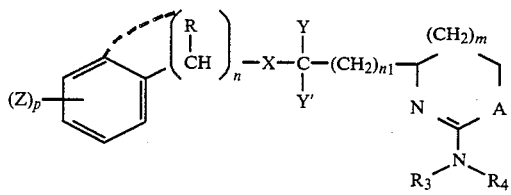

wherein Z is a hydrogen, a halogen, a lower alkyl radical, a lower alkoxy radical, a trifluoromethyl a trifluoromethoxy, a cyano group, a nitro group, a carboxamido group, a lower alkenyl radical, a lower alkylthio, a lower alkyne dioxy, a lower cyclo alkenyl radical or a lower cycloalkyl radical
X is an oxygen, a sulphur atom or an iminogroup of the formula $>N-R_1$ wherein $R_1$ is a hydrogen, a lower alkyl radical, an acyl residue derived from an organic carboxylic or sulphonic acid; a methylene group or a direct bond Y is a hydrogen, a lower alkyl radical, a phenyl radical, a substituted phenyl radical, a hydroxy or a phenoxy radical
Y' is a hydrogen
or Y and Y' together are an oxygen
or Y forms with the adjacent phenyl ring, when R is zero, a bicyclic-homo- or heterocyclic, saturated or unsaturated structure
A is a group NH or a sulphur atom
$R_3$ and $R_4$ the same or different, are hydrogen, a lower alkyl radical, a lower alkenyl radical, an aryl lower alkyl radical,
a heteroaryl lower alkyl radical, an aryl, an alcoyloxycarbonyl group, an acyl residue from an organic carboxylic acid having from 1 to 10 carbon atoms or an amino group
or $R_3$ and $R_4$ together form with the nitrogen atom to which they are bound, an alkylene chain optionally including one or two extra hetero atoms
R is a hydrogen, a lower alkyl radical, a phenyl radical which may be substituted or a phenylene radical linked to the adjacent phenyl ring by an alkylene chain having 1 or 2 carbon atoms
n is zero or 1
$n_1$ is zero, 1 or 2
m is zero, 1 or 2
p is 1, 2 or 3 and the dotted line symbolizes an optional carbon-carbon double bond.

This invention also provides the acid addition salts thereof with a mineral or organic acid, preferably a therapeutically compatible acid. This invention further includes the tautomeric imino forms of the compounds of formula I. Due to the delocalization of the intracyclic double bond in the nitrogenous ring, the compounds of formula I in which at least one of the substituents $R_3$ and $R_4$ are hydrogen, may be represented in the form of an imino derivative having the formula I'

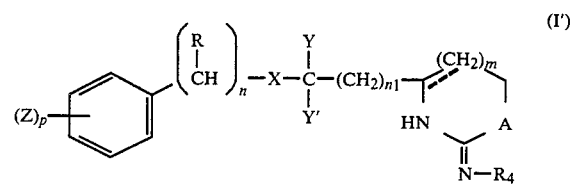

in which the substituants Z, p, R, X, Y, Y', $R_4$, n, m and $n_1$ remain defined as above-given.

The amino (I) form and the imino (I') form may coexist at the same time or the two tautomeric forms may be obtained distinctly either in the free form or in the salified form. This invention also provides to the optically-active isomers of a compound of formula I when containing at least one chiral atom, namely when Y and Y' are different.

Among the compounds of formule I they may more precisely be cited:
the compounds having the formula I"

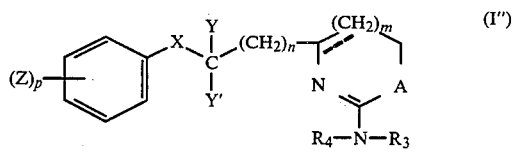

which correspond to the case where n is zero and X is oxygen, sulphur or an imino group of the formule $>NR_1$, wherein
$R_1$ is hydrogen, a lower alkyl radical; a methylene group or a direct bond
the compounds of formula I'''

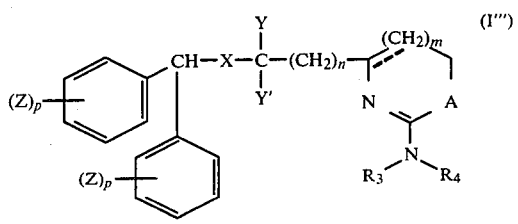

wherein the definitions of the substituents remain unaltered
the compounds of formula I''''

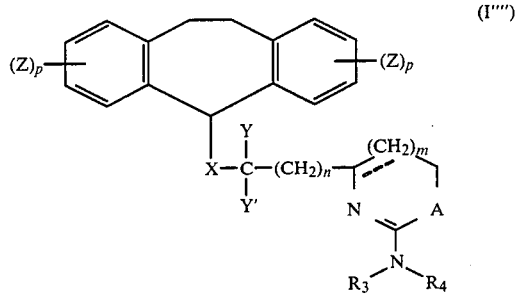

in which Z, X, Y, Y', R₃, R₄, A, m, n₁ and p have the same meaning as above-indicated and particularly
The imidazolines of formula $I_A$

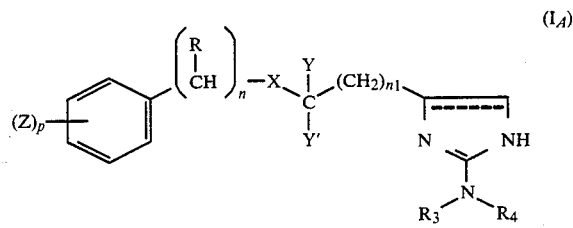

The tetrahydropyrimidines of formula $I_B$

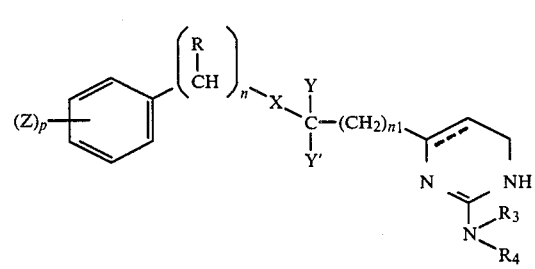

The 2-amino-thiazoles of formula $I_C$

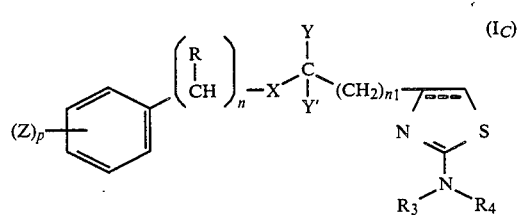

wherein the substituents Z, R, X, Y, Y', R, R₃, R₄, p, n and n₁ in the various formulas have the above-indicated definitions as well as their acid addition salts with a mineral or organic acid.

Among the physiologically compatible acid addition salts, it may be cited the hydrochlorides, the hydrobromides, the sulphates, the nitrates, the phosphates, the sulfites, the acetates, the butyrates, the caproates, the suberates, the succinates, the tartarates, the citrates, the itaconates, the glutamates, the aspartates, the benzoates, the trimethoxy benzoates, the salicylates, the niflumates, the flufenamates, the mefenamates, the nicotinates, the isonicotinates, the benzene sulphonates, the methane sulphonates, the ethane sulphonates, the isethionates, the para-holuene sulphonates, the naphtalene sulphonates, the glucose-1-phosphates or the glucose 1,6-diphosphates. The acids which may not be used for the therapy may be used as a means for isolating, purifying or resolving the compounds of formula I.

In this respect, it may be cited the perclorates, the iodates, the bromates, the vanadates or the chromates; the salts with strychnic acid, d-chrysanthemic acid, indolyl-3 acetic acid dichlorophenoxy isobutyric acid or citraconic acid.

As far as this invention is concerned, the word lower alkyl is intended to designate a hydrocarbon radical having from 1 to 6 carbon atoms in straight or branched chain. Examples of such radicals are the methyl, ethyl, isopropyl, secbutyl, tert butyl, neopentyl or n-hoxyl.

A lower alkoxy radical includes an alkyl radical defined as above. Among the halogen atoms it may more particularly be cited the fluorine and chlorine. However, the bromo or iodo derivatives are about of the same interest.

A lower alkenyl radical is a hydrocarbon radical having a double bond, including from 2 to 6 carbon atoms. It may be cited as examples of lower alkenyl radicals, an allyl radical, a methallyl radical, a but-2 enyl radical, an isopropenyl radical or a 3-methyl but-1-enyl radical.

An alkylenedioxy radical has from 1 to 4 carbon atoms in the alkylene chain as for example methylenedioxy or ethylene dioxy.

When Y is a substituted phenyl radical, the substituents are one to three halogen atoms a trifluoromethyl radical or a trifluoromethoxy radical, one to three lower alkyl radicals or one to three lower alkoxy radicals.

When Y forms with the adjacent phenyl ring a bicyclic structure, the resulting compounds have the formula $I_E$

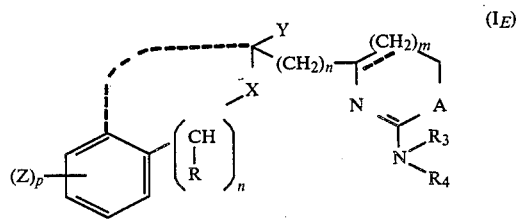

wherein X have the above-given definitions
Y' is hydrogen or hydroxy
and Z, R₃, R₄, A, m, n, p are defined as previously as examples of such bicyclic structures the compounds of formula

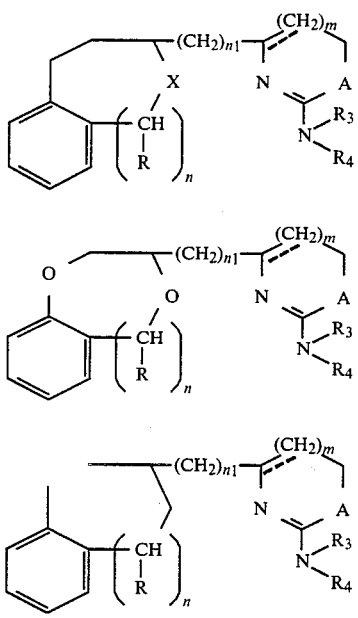

wherein X is oxygen, sulphur or >N-R₁ and n is 0 or 1.

Accordingly these bicyclic structures are those of benzodioxan tetrahydroquinoleines, tetrahydronaphtalene, dihydronaphtalene, or a benzimidazole.

These bicyclic structure may include further degree of insaturation such as for example a naphtyl-1 a naphtyl-2 ring.

An aryl lower alkyl radical is a mono cyclic aryl radical bearing a hydrocarbon chain having from 1 to 6 carbon atoms in straight or branched chain. Examples of such aryl lower alkyl radical are the benzyl, phenethyl, α-methylphenetyl, 2-6-dichlorobenzyl or 2,3,5-trimethoxybenzyl radicals.

A hetero aryl lower alkyl radical is a hetero cyclic aromatic radical bearing a hydrocarbon chain having from 1 to 6 carbon atoms. Examples of such radical are the pyridyl-2-methyl, the furyl-ethyl, the pyranylethyl or the thienyl-2methyl radical.

When R₃ and R₄ are together an alkylene chain, the resulting cyclic structure has from 4 to 7 carbons such as azetidine, pyrolidine, piperidine or hexamethylene imine. When this chain is interrupted by one or two extra hetero atoms, the resulting ring is for example a tetrahydropyrimidine, a tetrahydro-oxazine, a morpholine, a thiazine, a pyrazolidine or a piperazine ring. These rings may further be substituted such as with lower alkyl radicals hydroxy lower alkyl radicals, pyridyl, phenyl substituted phenyl radicals, or pyrimidyl.

When R₃ or R₄ is an acyl residue, it may derive from an aliphatic acid such as the acetyl radical, the propionyl, the dipropylacetyl radical; or from an aromatic acid such as the benzoyl, the naphtoyl-1, the 2,6-dichlorobenzoyl, the 3,4,5-trimethoxybenzoyl, the veratroyl, the syringoyl, the O-carbethoxy tyringoyl, the nicotinoyl or the furoyl radicals; or from an aryloxy alkanoic acid such as phenoxy acetic acid, dichlorophenoxy acetic acid or p-chlorophenoxy isobutyric acid.

This invention also extends to a process for producing the compounds of formula I wherein m is equal to zero which consists in condensing an epihalohydrin of formule II

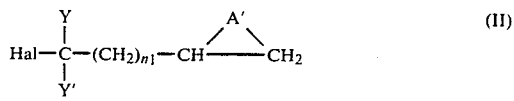

wherein A' is oxygen or sulphur
and Hal is chlorine or bromine
and the sulstitments Y, Y' and n₁ have the above given definitions
with an aromatic derivative of formula III

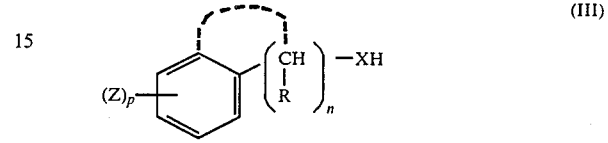

wherein the substituents R, Z, n, p and X are defined as previously given
producing an aryl alkylated derivative of the formula IV

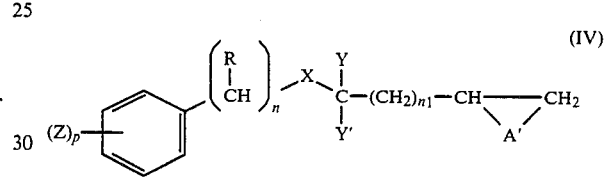

wherein the definitions of the substituents R, A', X, Y, Y', Z, n, n₁ and p remain unaltered
opening the oxiran ring by means of an alkali metal azide to produce the corresponding mono azide of formula V

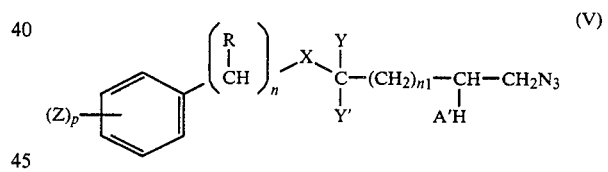

wherein the substituents R, A', X, Y, Y', Z, n, n₁ and p are defined as above given
submitting the latter when A is oxygen to the action of a functional derivative of a sulphonic acid of formula VI $R_2SO_2R_5$ (VI)

wherein $R_2$ is a substituted or unsubstituted alkyl radical or a mono- or bicyclic aromatic radical
and $R_5$ is a lower alkyloxy group or a halogen atom in the presence of a tertiary base to produce an azido ester of formula VII

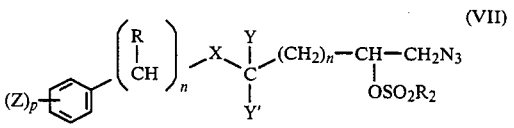

wherein the substituents X, Y, Y4, Z, n, p and $R_2$ have the above-given definitions reacting this ester with an alkali metal azide or thio cyanate in a polar solvent to obtain an azido derivative of formula VIII

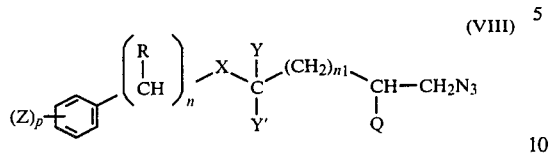
(VIII)

wherein the definition of the substituents R, X, Y, Y', Z, n n₁ and p remain unaltered and Q is a SH radical or an azido radical which is reduced by hydrogenation in the presence of a catalyst to an amino ethane derivative of the formula IX

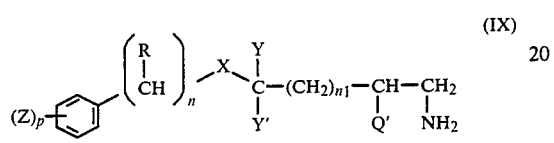
(IX)

wherein the substituents R, X, Y, Y', Z, n, n₁ and p have the above given definitions.

and Q' is a SH radical or an amino group/condensing the latter with a carbo iminating reagent selected from the group consisting of a cyanogene halide and a S-methyl isothiouronium halide of the formula

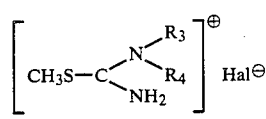

and recovering a compound of formula I wherein R, X, Y, Y', Z, n, n₁ and p have the above given definitions A is a sulphur or an imino radical and R₃ and R₄ are both hydrogen when the cyano iminating reagent is a cyanogen halide or R₃ and R₄ are hydrogen, and/or a lower alkyl a lower alkenyl, an aryl lower alkyl, a hetero lower alkyl, an aryl, an alkoxy carbonyl or an acyl radical from an organic carboxylic acid having 1 to 10 carbon atoms or R₃ and R₄ are together with the nitrogen atom an alkylene chain when the carbo iminating reagent is a S-methyl isothio uronium halide which may be further salified by adding a mineral or organic acid or resolved into their optically-active isomers by reacting with a chiral reagent.

This invention also includes a process for preparing the compounds of formula I in which an aromatic derivative of formula V is condensed on allyl halide to produce an alkenylated compound of formula X

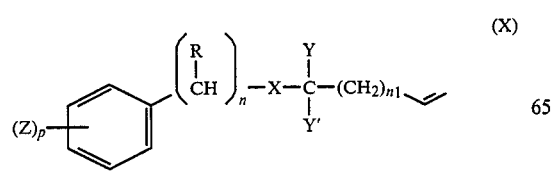
(X)

wherein Z, p, R, n, Y, Y' and n₁ are defined as above, brominating the latter with bromine to produce a dibromo derivative of formula XI

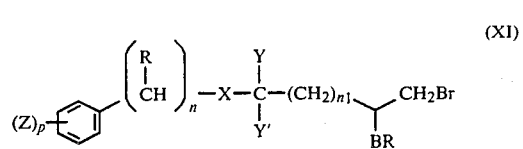
(XI)

wherein Z, R, Y, Y', X, n, n₁ and p are defined as above reacting the latter with an alkali metal azide to produce the di-azido derivative of formula VIII

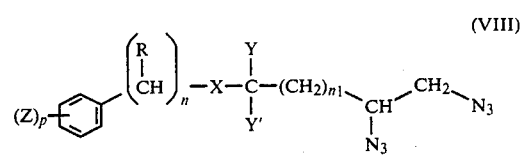
(VIII)

which is hydrogenated in the presence of a catalyse into a diamino derivative of formula IX

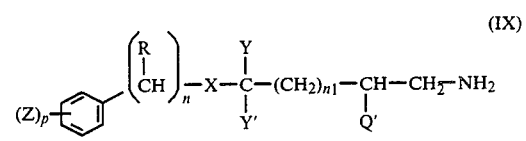
(IX)

and cyclising this derivative by means of carbo iminating reagent such as a cyanogen bromide into a imidazolic derivative of formula I_A

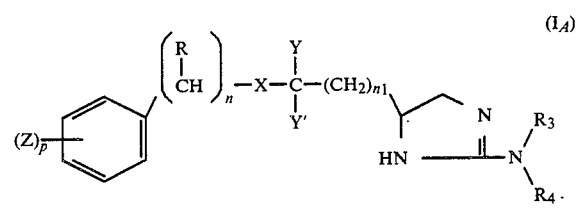
(I_A)

wherein the definitions of the substituents R, Z, X, Y, Y', R₃, R₄, n, n₁ and p are defined as above.

This invention further encompasses another process for producing the compounds of formula I which comprises (a) condensing an aryloxyalkyl aldehyde of formula XII

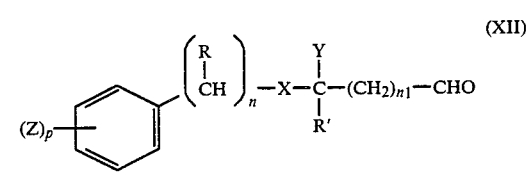
(XII)

wherein the substituents R, X, Y, Y', Z, p and n are defined as above with an alkali metal cyanide in the conditions of the Strecker's reaction to produce an αcyano amine of the formula XIII

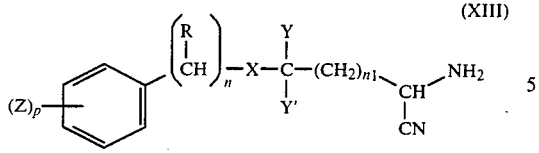 (XIII)

wherein the substituents R, Z, Y, Y', n, n₁ and p are defined as previously given (b) reducing the latter by hydrogenation in the presence of a catalyst into a substituted diamino ethane of formula IX

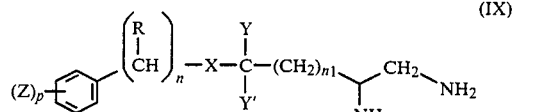 (IX)

wherein the definitions of the substituents R, X, Y, Y', Z, n, n₁ and p remain unaltered (c) condensing this compound with a cyano iminating reagent to produce a cyclic derivative of formula $I_A$.

In order to produce a compound of formula I wherein $R_3$ and/or $R_4$ are an acyl radical, an alkyl radical, an alkenyl radical, an aryl radical or an aralkoyl radical, it may be used a process which comprises the steps of condensing a diamino ethane of formula IX

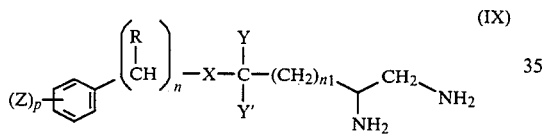 (IX)

wherein the meanings of the substituents Z, p, R, X, Y, Y', n and n₁ remain those previously given with carbon disulfide to produce an imidazoline thione of formula XIV

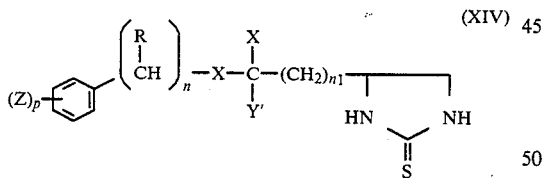 (XIV)

wherein the definitions given to the substituents Z, p, R, n, X, Y, Y' and n₁ remain unaltered submitting the latter to an alkylating agent to produce an alkylthio imidazolinium salt of formula XV

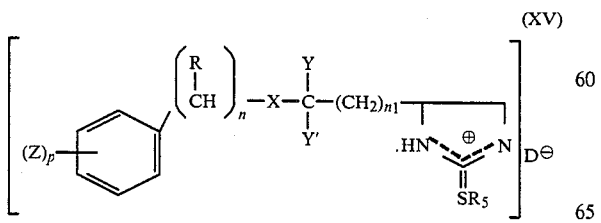 (XV)

wherein the substituents keep the above given definitions $R_5$ is a lower alkyl radical and D is mineral or organic anion, salifying the base condensing the latter with an amine of the formula XVI

 (XVI)

wherein $R_3$ and $R_4$ are defined as previously with the proviso they are not at the some time hydrogen and producing a compound of formula $I_A$

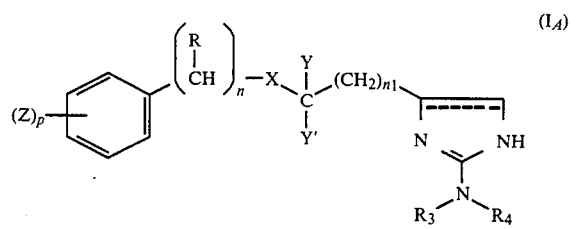 ($I_A$)

wherein $R_3$ is hydrogen, a lower alkyl radical, a lower alkenyl radical, an aryl lower alkyl radical, a (heteroaryl) lower alkyl radical, an aryl, an alkyloxy carbonyl group, an acyl radical derived from an organic carboxylic acid having from 1 to 10 carbon atoms $R_4$ is a lower alkyl radical, a lower alkenyl radical, an aryl lower alkyl radical, a (heteroaryl) lower alkyl radical, an aryl, an alkyloxycarbonyl, an acyl residue derivated from an organic carboxylic acid having from 1 to 10 carbon atoms or $R_3$ and $R_4$ are together with the nitrogen atom to which they are bound, the alkylene chain of a heterocyclic ring, optionally including one or two further hetero atoms.

To produce 2-acylamino derivatives of formula I, it may be also possible to let a functional derivative of an alkyl, aryl or arylalky carboxylic acid react with a 4,5-dihydro [1H] imidazole of formula XVII

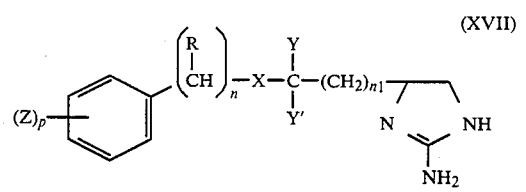 (XVII)

wherein the definitions of the substituents Z, p, R, n, X, Y, Y' and n₁ remain unaltered according to the conditions of the Schotten-Baumann's reaction.

The compounds of formula $I_A$ wherein A is a group >NH and the dotted line symbolizes a double bond may be obtained according to a process which comprises the steps of oxydizing and 1-azido 3-aryloxy 2-propanol of formula V

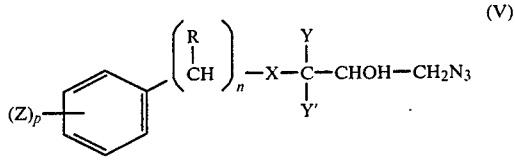

(V)

wherein Z, p, R, y, Y', R and n have the above given definitions and X is oxygen or sulphur or a radical >N-$R_1$ ($R_1$ being defined as previously)

by means of a metallic oxydizing reagent in acidic medium to produce an azido ketone of formula XVIII

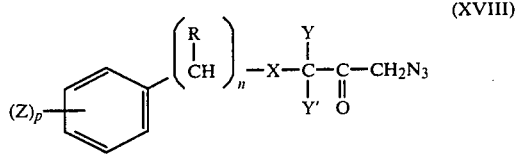

(XVIII)

wherein Z, p, R, Y, Y' and X have the above-given definitions reducing the latter by catalytic hydrogenation into an amino ketone of formula XIX

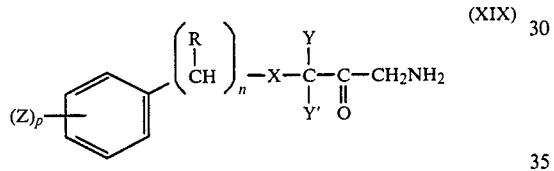

(XIX)

wherein the definitions of the substituents Z, p, R, n, X, Y, Y' remain unaltered and condensing this ketone with cyanamid in the presence of an alkaline base to produce an imidazolinic derivative of formula $I_A$

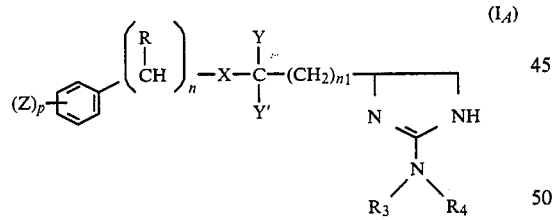

($I_A$)

wherein the substituents Z, p, R, n, X, Y and Y' are defined as previously given which may be salified by adding a mineral or organic acid or acylated by means of a functional derivative of an organic carboxylic acid or resolved into its optically active isomers by means of an optically-active acid or alkylated by means of an alkylketone or an alkyl aldehyde in the presence of a reducing agent.

According to the most preferred features, the processes according to this invention may be defined as follows:

(1) The condensation of the epihalohydrin of formula II with the aromatic derivative of formula III is carried out in a polar inert solvent such as for example acetonitrile in the presence of a hydracid acceptor such as for example sodium carbonate and potassium carbonate.

(2) The opening of the oxiran ring is performed by means of an alkali metal azide in an aqueous medium such as for example a mixture water-acetone, or a mixture water-acetonitrile or a mixture water-dimethyl formamide.

(3) The functional derivative of the sulphonic acid VI is preferably an alkyl sulphonyl halide such as methane sulphonyl chloride ethane sulphonyl chloride, trifluoromethyl sulphonyl chloride—or an aryl sulphonyl halide such as for example benzene sulphonyl halide, p.toluene sulphonyl halide, or naphtylsulphonyl halide. The condensation is performed in the presence of a tertiary base such as triethyl amine, pyridine or collidine.

(4) The conversion of the sulphonate into an azide is performed in a polar aprotic solvent such as for example dimethylacetamide, dimethyl formamide, acetonitrile or hexamethyl phosphorotriamide.

(5) The hydrogenation of the azido- or di-azido derivative is performed in the presence of a catalyst such palladium, or platinum or an inert carrier such as char coal, baryum sulphate, or strontiam carbonate.

(6) The condensation of the aromatic derivative III with an allyl halide is performed in a polar solvent such as acetonitrile, in the presence of a basic reagent such as sodium carbonate or potassium carbonate.

(7) The bromation of the alkenylated derivative X is performed by means of bromine dissolved in an inert solvent such as for example carbon tetrachloride.

(8) The conversion of the dibrominated derivative into a diazido derivative is performed by heating the dibrominated derivative with an alkali metal azide in a polar solvent, such as dimethyl formamide or dimethyl sulfoxide.

(9) The cyclisation of the diaminated compound IX is performed by means of cyanogen bromide in an inert solvent such as an aromatic hydrocarbon at a temperature lower than 30°.

(10) The cyclisation of the diaminated IX is performed by means of a S-methyl isothiouronium halide, heating in an inert high boiling solvent such as isopropanol, propanol, collidine or xylene.

(11) The complete synthesis of the compounds of formula I may also be carried out starting from an already resolved raw material, coming from a natural product which has been conveniently transformed such as d-mennitol or l-ascorbic acid.

Similarly, the epoxides of formula IV may be resolved into their geometric isomers and be converted by the further steps of the synthesis into the corresponding diastereo iisomer.

The resolving agent is preferably an optically active acid such as d-tartaric acid, NN-diethyl d-tartranine acid, d-camphoric acid, 1-cetogulonic acid, abietic acid, pimaric acid or d-camphosulphonic acid.

It may also be used the physico-analytical means such as for example high pressure liquid chromatography (HPLC), or chromatography on a column filled with an optically-active carrier.

Moreover, it may be used for the resolution an enzymatic reagent such as amylase or a hydrolase, a hydroxy function being previously esterified. A hydroxy function may also be esterified by an optically-active acid such as d-camphonic acid, the epimeric esters thereof are separated then saponified into an optically active ester.

This invention also extends to the pharmaceutical compositions having as active ingredient at least one compound of formula I or an acid addition salt thereof with a mineral or organic acid in conjunction or admixture with an inert non-toxic pharmaceutically acceptable carrier or vehicle.

The pharmaceutical compositions may further incorporate another active ingredient having a synergistic or complementary action.

Preferably, the carrier or the vehicle is one of those suitable for the parenteral, oral, rectal sublingual, percutaneous or permucous way of administration.

Among the suitable pharmaceutical forms, it may more particularly be cited the uncoated or coated tablets, the dragees, the pills, the soft gelatine capsules, the cachets, the capsules, the injectable or drinkable solutions, the drinkable suspensions, the syrups, the suppositories, the solutions for percutaneous use, and the sublingual tablets. The carriers or vehicles are for example the starches, the celluloses or the chemical derivatives of cellulose such as ethyl cellulose or hydroxypropyl cellulose; carboxymethylamidon or the alkali metal salts thereof, magnesium phosphate, calcium carbonate, talc or magnesium stearate, water or saline solutions, syrup of sugar, syrup of arabic gum, cacao butter, polyethylene glycols, polyethylene glycol stearates. The compounds of formula I and the salts thereof exhibit interesting pharmacological properties. They show namely anti-depressive properties and cardio-vascular properties due to some effects of the adrenergic type. More particularly the compounds of formula I and the salts thereof show positive inotropic and/or chronotropic effects. Moreover, some of them have antimicrobial and/or antiparasitic and/or antifungic properties against pathogene microbes of fungic or against noxious worms.

Accordingly, the compounds of formula I have a therapeutic use in human therapy as a drug for alleviating the acute or chronic cardio-vascular failure more precisely in the shock conditions, and as a psychotropic drug useful against the depressive conditions from endogenous or behavioural origin.

The useful dosology may vary depending the weight, the age of the patient, the route of administration and the therapeutic use. It ranges from 1 to 500 mg per unit dosage in the man and from 5 to 1000 mg per day in the man.

The following examples illustrate the invention. They do not limit it in any manner.

EXAMPLE I 4-(O.chlorophenyloxymethyl) 2-amino 4, (-dihydro 1H Imidazole and its hydrobromide.

Step A. 1-0-chlorophenyloxy 2,3-epoxy propane/62,2 ml o.chlorophenol are dissolved in 500 ml acetonitrile and to this solution 248, 4 g potassium carbonate and 0.5 g potassium iodide are added. After 30 mn stirring at room temperature, 140 ml epichlorhydrin are added dropwise. The whole mixture is heated to reflux for 15 hours. After the usual measures 60, lg of a colourless liquid is recovered by distillation. It boils at 85° C. under $2.10^{-2}$ mm Hg.

Step B. 1.(o.chlorophenyloxy) 3-azido propopanol-2. To a solution of 51,7 g of epoxide of step A in 300 ml acetonitrile, 27.3 g sodium azide previously dissolved in 15 ml water are added. The mixture is heated to reflux for 4 hours. After the usual purifications, 61,17 g of a clear yellow liquid are obtained. The yield amounts to 96.4%. On silicat gel plates Rf=0.43 using a mixture toluene 9:tetrahydrofuran 1 as the cluting solvent.

Step C. 1-O.chlorophenyloxy 3-azido 2-tosyl oxypropane 61.17 g of the azide of step B are dissolved in 300 ml pyridine cooled to $-10°$ and to this solution a solution of 66.7 g tosyl chloride in 300 ml pyridine is added for 1 hour while keeping the inner temperature between $-5°$ C. and $-2°$ C. The mixture is kept for 48 hours at 4° C. then poured on a mixture ice-water. The resulting precipitate is taken up in toluene and purified as usual. 90.1 g of a yellowish solid is obtained. Yield 87.4%.

On silica gel plates Rf=0.63 using the mixture tetrahydrofuran 1/Toluene 9 as the eluting solvent.

Step D. 1-(O.chlorophenyloxy) 2,3-diazido propane. 9.3 g of the tosyloxy derivative of step C are dissolved in 30 ml dimethyl formamide and to this 3.9 g sodium azide are added. The mixture is kept under stirring for 30 mn at room temperature then 4 hours at 90° C. The resulting solution is poured in water and extracted with ether. After the usual purifications, 6.06 g of a slightly orange liquid are recovered. The yield amouants to 100%. On silica gel plates Rf=0.52 using the mixture petroleum ether 1/ethyl ether 1 as the eluting solvent.

Step E. 1-(O.chlorophenyloxy) 2,3-diamino propane. In a closed flask 49.77 of the diazido derivative, 250 ml ethanol and 10 g palladium on charcoal at 5% are added. The flask is purged by a stream of nitrogen then hydrogen is bubbled under strong stirring. The performance of the hydrogenation precedure is followed by TLC. The palladium on charcoal is thereafter filtered and 40.13 g of a brown coloured liquid are obtained. Purification is carried out by treatment with hydrochloric acid (dihydrochloride) then with base. 28 g of the free base of 1-(o.chlorophenyloxy methyl) 2,3-diamino propane are recovered. Yield: 70.8%.

Step F. 4-(O.chlorophenyloxymethyl) 2-amino 4,5-dihydro [1H] imidazole and its hydrobromide.

To a solution of 11.32 g 1-(O.chlorophenyloxymethyl) 2,3-diaminopropane in 160 ml toluene one adds drop by drop a solution of 6.46 g cyanogene bromide in 60 ml toluene. The temperature must remain lower than 30° C. Stirring is kept for 5 hours at room temperature. After separation by filtration of the thus produced solid and usual purifications, 8.4 g of the pure hydrobromide are obtained as a colourless powder melting at 132° C. Yield=49%.

EXAMPLE II 4-(phenoxymethyl) 2-phenylamino 4,5-dihydro [1H] imidazole and its fumarate.

7 g of 1-phenoxy 2,3-diamino propane as the dihydrochloride, 8.55 g of S-methyl phenyl isothiouronium and 8.8 g triethylamine previously dissolved in 50 ml propanol are heated to 140° in a reactor for 12 hours. After usual purifications, a strongly coloured oil is recovered. It is purified by chromatography on a column filled with alumina and eluting after fixation with a mixture of methylene chloride 95—methanol 5—The eluates are treated with a solution of fumaric acid in ethanol giving rise to the formation of the fumarate which is purified by treatment with a mixture ethanol—ether—2.25 g of a colourless powder are thus obtained melting at 174° C.
Yield =23%.

EXAMPLE III 4-benzyloxy 2-ethylamino 4,5-dihydro [1H] imidazole.

Step A: 3-benzyloxy prop 1-ene. To a mixture of 432 mg benzylic alcohol and 31.75 copper powder heated to 40°, 153 g redistalled allyl chloride are dropwise added. The mixture is kept at the reflux for 4 hours while adding some time to time sodium carbonate. After filtration to emiminate the mineral matters and usual purifications, the resulting liquid is chromatographed on a silica column. After fixation the desired product is eluted using the mixture petroleum ether 5—ethyl ether 95 66 g of the pure compound are thus obtained. Yield=44.6%.

Step B. 1-benzyloxy 2,3-dibromopropane.

162.5 g of 3-benzyloxyprop-lene are dissolved in 1000 ml carbon tetrachloride cooled to 0° and 56.5 ml bromine in 100 ml carbon tetrachloride are dropwise added while keeping the temperature at about 0°.

After the usual measures, a yellow oily product is recovered and used as such for the next steps of the synthesis.

The yield in raw product amounts to 98%.

Step C. 1-benzyloxy 2,3-diazidopropane.

50 g of the dibromo derivative of step B are dissolved in 300 ml dimethyl formamide and to this 26.4 g sodium azide are added. The whole mixture is kept under stirring for 12 hours while heating at 80°. Water is thereafter added and the residue is purified as usual. 31.45 g of an oily yellowish-coloured residue are recovered.

The yield amounts to 83.5%.

Step D. 1-benzyloxy 2,3-diaminopropane.

Using the method shown in example I step E and starting from 1-benzyloxy 2,3-diazido propane the 1-benzyloxy 2,3-diamino propane is obtained.

Step E. 4-benzyloxy 2-ethylamino 4,5-dihydro[1H]imidazole and its hydrochloride.

7.5 g of 1-benzyloxy 2,3-diaminopropane as the dihydrochloride, 8.1 g of S-methyl ethyl isothio uronium iodide and 8.8 g triethylamine dissolved in 50 ml propanol are heated together at 140° in a reactor for 12 hours. After reversion to room temperature, the mixture is distilled off. The oily residue is purified by chromatography on silica gel column. The eluate is dissolved in 25 ml ether and saturated with a stream of hydrochloric acid. The hydrochloride progressively precipitates. It is kept for a night in a cool place then the crystalls are separated which are dried and rinced with few ml of ether. After drying in an oven, 4.45 g 4-benzyloxy 2-ethylamino 4,5-dihydro[1H]imidazole are obtained as the hydrochloride.

EXAMPLE IV 4-(p. chlorobenzyloxymethyl) 2-(N-carbethoxy amino) 4,5-dihydro[1H]amidazole.

10 g of S-methylisothio Urea sulphate are dissolved in 8 ml water and 3.6 ml ethyl chloroformate are added thereto.

The mixture is cooled to about 5° C. and 5.5 ml sodium hydroxide at 20% are added. The stirring is kept for 5 hours at room temperature. After usual purifications, the resulting compound as a pale yellow oil is added to 3.5 g 2,3-diamino 1-(p. chlorophenoxymethyl) propane as the hydrochloride and to 2.14 g sodium bicarbonate in 100 ml methanol. Methanol is distilled off then replaced with 150 ml n-propanol and the whole mixture is heated to reflux for 10 hours. The usual purifications supply with 2.17 g of a solid melting at 191° C. (hydrochloride). Yield=54%.

All the described compounds have IR spectra and RMN spectra in accordance with the indicated structures.

EXAMPLE V 4-(benzodioxanyl-2) 2-amino imidazoline and its hydrobromide as well as their threo and erythro isomers.

Step A. 2-(benzodioxanyl-2) 2-hydroxy 1-azido ethane.

Starting from 2-(benzodioxanyl-2) 2-hydroxy 1-bromo ethane and sodium stream dissolved in dimethyl formamide at a temperature of about 80° C., 2-(benzodioxanyl-2) 2-hydroxy 1-azidoethane is obtained.

Step B. Using the same procedure as in example I step C, starting from 2-(benzodioxanyl-2) 2-hydroxy 1-azido ethane and p. toluene sulphonyl chloride, 2-(benzodioxanyl-2)2-p. toluene sulphonyloxy 1-azido ethane is obtained.

Step C. Using the same procedure as in example I step D, 2-(benzodioxanyl-2) 2(p.toluene sulphonyloxy) 1-azido ethane is converted into 2-(benzodioxanyl-2) 1,2-diazido ethane which allows the separation of the isomers erythro and threo by chromatography on a column filled with silica.

Step D. Using the same procedure as in example V step E, and starting from 2-(benzodioxanyl-2) 1,2-diazido ethane as the mixture of isomers erythro and threo or in the resolved form-2-(benzodioxanyl-2) 1,2-diamino ethane is obtained.

Step E. Using the same procedure as in example I step F, and starting from 2-(benzodioxanyl-2) 1,2-diamino ethane and cyanogene bromide, 2-amino 4-(benzodioxanyl-2) imidazoline is obtained. This compound is further purified by converting it into its hydrobromide.

| MW | MP |
|---|---|
| (base) | (hydrobromide) |
| 219.25 | 225 |
| 219.25 | 180 |

| Analysis | | | | | | |
|---|---|---|---|---|---|---|
| Theoretical | | | Found | | | |
| C | H | N % | C | H | N % | |
| 44,01 | 4.7 | 13.99 | 44.06 | 4.81 | 13.81 | isomers erythro |
| 44.01 | 4.7 | 13.99 | 43.89 | 4.82 | 13.72 | threo |

EXAMPLE VI

Using the same procedure as in example III, the following compounds have been prepared.

(a) 4-(α-naphtyloxymethyl) 2-amino 4,5-dihydro[1H]imidazole as the hydrobromide MP=175° C.

MW of the base=214.295

| Theoretical | | | Found | | |
|---|---|---|---|---|---|
| C | H | N % | C | H | N % |
| 52.19 | 5.01 | 13.04 | 51.98 | 4.92 | 12.90 |

(b) 4(β-naphtyloxymethyl) 2-amino 4,5-dihydro[1H]imidazol melting at 194° C. as the hydrobromide.

MW of the base=241.295

|  | Theoretical |  |  | Found |  |  |
|---|---|---|---|---|---|---|
|  | C | H | N % | C | H | N % |
|  | 52.19 | 5.01 | 13.04 | 52.32 | 5.11 | 12.98 |

(c) 4-(2-methyl 4-bromophenoxy) 2-amino 4,5-dihydro[1H]imidazole.

isolated as the hydrobromide melting at 190° C.

|  | Analysis | | |
|---|---|---|---|
|  | C | H | N % |
| Theoretical | 36.19 | 4.14 | 11.51 |
| Found | 35.34 | 4.39 | 11.46 |

(d) 4-(2-methylphenoxy) 2-amino 4,5-dihydro[1-H]imidazole isolated as the hydrobromide melting at 125° C.

EXAMPLE VII 4-(2,2-diphenylethyl-1) 2-amino[1H]4,5-dihydro imidazole.

This compound has been prepared starting from 4-4-diphenylbut 1-ene previously described in the French patent No. 2.313.022, and converting it into the dibromo derivative, the diazido derivative, the diamino derivative, then cyclizing it by means of cyanogene bromide.

This compound is obtained as the hydrobromide which melts at 175° C.

| Analysis: $C_{17}H_{19}N_3,BrH$ = 265.31 | | | |
|---|---|---|---|
|  | C | H | N % |
| Theoretical | 58.95 | 5.82 | 12.13 |
| Found | 59.11 | 5.95 | 12.10 |

EXAMPLE VIII

4-[(N-phenyl N-p.toluenesulphonylamino)methyl]2-amino [1H]4,5-dihydro Imidazole.

This compound is obtained starting from N-phenyl N-allyl p. toluene sulphonamide (described in Zhur. Organ. Khimii (1965) 918) through the dibromo derivative, the diazido derivative, the diamino derivative which is cyclized by means of cyanogene bromide. The imidazole is isolated as its hydrobromide which crystallizes with 5 mol water-MP=126°-127°

| Analysis: $C_{17}H_{19}N_4SO_2,BrH,\frac{1}{2}OH_2$ = 344.43 | | | |
|---|---|---|---|
|  | C | H | N % |
| Theoretical | 47.01 | 5.10 | 12.89 |
| Found | 47.32 | 6.07 | 12.84 |
|  | 47.45 | 5.98 | 12.82 |

EXAMPLE IX

[Dibenzo (a,d) [5H]10,11-dihydrocyclohepten-5 yl]4-methyl 2-amino[1H]4,5-dihydro imidazole.

This compound is obtained as its hydrobromide, starting from 5-allyl [dibenzo (a, d) [5H]10,11-dihydro cycloheptene] (described in the Belgian patent No. 633.597) and converting it into its dibromo derivative, its diazido derivative, its diamino derivative which is finally cyclized into the corresponding imidazole.

The hydrobromide crystallizes with ½ mol water.
MP higher than 55° then decomp.

| Analysis: $C_{19}H_{23}N_3,BrH,\frac{1}{2}H_2O$ = 291,41 | | | |
|---|---|---|---|
|  | C | H | N % |
| Theoretical | 60.32 | 5.95 | 11.10 |
| Found | 60.48 | 5.96 | 11.22 |

EXAMPLE X

4-[(2-nitrophenoxy)phenyl methyl][1H]4,5-dihydro imidazole

This compound has been prepared starting from ethyl 2-nitrophenoxy 3-phenyl 2-hydroxy propionate (described in J. of Heterocyclic Chem 20 (1983) 259) which is hydrogenated to the corresponding diol, conversion of the latter to the dimethane sulphonate, then to the diazide and finally to the diamino derivative which is cyclized by means of cyanogene bromide.

The hydrobromide melts at 237°.

EXAMPLE XI 4-phenoxymethyl 2-amino 1,4,5,6-tetrahydro pyrimidine.

Step A.

4-phenoxybutane 1,3-diol.

28 g (0,12 Mol) of ethyl 4-phenoxy 3-oxobutanoate are dissolved in 200 ml ethyl ether and to this solution it is added a suspension of 13.6 g lithium aluminohydride in 500 ml ethyl ether previously cooled to 0°. Sterring is kept for 2 hours at room temperature. The excess of reagent is destroyed by cautiously adding an aqueous solution of sodium sulphate. The precipitate is filtered and the filtrate is evaporated to dryness. The residue is taken up in petroleum ether from which it crystallizes. 20 g of the desired compound i.e. a yield of 92%. It melts at 52°-54°.

RMN spectrum (in CDCl₃) between 6.7 and 7.3. between 3.75 and 4

The diol is further converted into its ditosylate, then into the diazide, reduced into the diamino derivative and further cyclised in the tetrahydropyrimidine.

EXAMPLE XII 4-benzyl 2-amino [1H]4,5-dihydro imidazole the fumarate melts at 200°

| Analysis: $C_{10}H_{12}N_3$ = 231,257 | | | |
|---|---|---|---|
|  | C | H | N % |
| Theoretical | 62.33 | 5.67 | 18.17 |
| Found | 62.10 | 5.62 | 18.00 |

EXAMPLE XIII 4-(O.chlorophenoxymethyl) 2-N-morpholino 4,5-dihydro[1H]imidazole Step A. 4-(o.chlorophenoxymethyl) 2-thio 4,5-dihydro[1H]imidazoline 0,2 mol of 3-O-chlorophenoxy 1,2-diamino propane are dissolved in 400 ml of 80% ethanol. To this 12 ml carbon sulfide are dropwise added under a stream of argon. The mixture is heated to reflux for 1 hour. After reversion to room temperature 0.35 ml concentrated hydrochloric acid are added dropwise. The whole mixture is heated to reflux for 6 hours. After cooling an equal volume of water is added and the precipitate is separated. It is a yellow compound melting at 148°. It is purified by recrystallization from methylene chloride.

Yield=52%.

Step B. 4-(O.chlorophenoxymethyl) 2-methyl thio imidazolinium hydroiodide.

To 0.08 mol of the compound of step A 6.25 ml (i.e. 14.2 g) of methyl iodide are added. The mixture is heated to the reflux for 1 hour then concentrated to dryness. The formed residue is washed with ether, then dried giving rise to the recovery of 29.3 g of a yellow compound which melts at 174° C. After recrystallization from isopropanol the melting point is increased to 175°. The yield amounts to 94%.

Step C. 4-(O.chlorophenoxymethyl) 2-N-morpholino 4,5-dihydro [1H]imidazole.

6 g of the hydro iodide of step B are added to 2.7 g of morpholine in 100 ml isopropanol. The mixture is heated to reflux for 24 hours. After evaporation of the solvent, the residue is taken up with water and the aqueous phase is washed with ether. 10% sodium hydroxyde is then added until the medium is neutral and the phase is extracted with methylene chloride. The methylene solution is washed with water dried and evaporated off. The compound is purified by converting it into its fumarate by adding fumaric acid in ethanol. The fumarate is recrystallised from methanol.

It melts at 184° C. Yield=81%.

Similarly the other N-substituted amino imidazolines are obtained reacting the S-methyl thio derivative with the suitable amines in a solvent such as isopropanol at the reflux or at a temperature ranging from 80° to 140° C. in a reactor.

EXAMPLE XIV 4-(O.chlorophenoxymethyl) 2-benzoylamino 4,5-dihydro[1H]imidazole.

To a solution of 6 g of 4-(O.chlorophenoxymethyl) 2-amino 4,5-dihydro [1H] imidazole in 200 ml water, a N-solution of sodium hydroxide is added to a pH value of 10.5. Under strong stirring a solution of benzoyl chloride in toluene (3.5 ml benzoyl chloride in 20 ml toluene) is added to. The addition is made drop by drop and lasts about 2 hours while adding at the same time a N-solution of sodium hydroxide in order to keep the pH value between 7 and 9.

A white solid separates and the stirring is kept for 5 further hours. The solid is filtered, washed with water then with toluene then with ethyl acetate.

It is recrystallized from ethanol. The 2-benzoylamino derivative melts at 213°. Yield=49.6%.

EXAMPLE XV 4-benzyl 2-amino thiazole.

10 g of 1-chloro 3-phenyl propan-2-one are added to 3.9 g thiourea in 100 ml ethanol. The mixture is refluxed for 2 hours. After cooling the whole is concentrated under reduced pressure. The residue is taken up in diluted ammonia then extracted with ether. After purifications the so obtained solid is converted into its hydrochloride which melts at 127°. The yield is=79%.

| Analysis: $C_{10}H_{10}SN_2$ = 190.27 | | | |
|---|---|---|---|
| | C | H | N % |
| Theoretical | 52.98 | 4.89 | 12.36 |
| Found | 52.58 | 4.96 | 12.30 |

In the same manner they have been prepared the following compounds:

-4-(phenoxymethyl) 2-amino thiazole its methane sulphonate melts at 153°.

| Analysis: $C_{11}H_{14}N_2O_4S_2$ = 302,37 | | | |
|---|---|---|---|
| | C | H | N % |
| Theoretical | 43.69 | 4.67 | 9.26 |
| Found | 43.86 | 4.78 | 9.20 |

4--(phenoxyethyl) 2-aminothiazole the hydrochloride of which, melts at 174°.

| Analysis: $C_{11}H_{13}ClN_2OS$ = 256,75 | | | |
|---|---|---|---|
| | C | H | N % |
| Theoretical | 51.46 | 5.10 | 10.91 |
| Found | 51.36 | 5.21 | 10.98 |

Further compounds which have been shown in the annexed tables have also been prepared.

EXAMPLE XVI

Pharmacological Study of the Compounds of this Invention

The compounds of formula I are endowing with an interesting pharmacological profile.

(1) They exert more particularly antidepressive action, namely shown in the antagonist tests of hypothermia and ptosis caused by reserpine, the tests of hypothermia caused by apomorphine (the compounds of formula I are active at doses ranging from 50 to 200 mg/kg by oral way), and in the test of desperance in the mice (wherein the compounds are active at doses ranging from 20 to 40 mg/kg by intraperitoneal way). These anti-depressive effects of the compounds of formula I are not connected with any anti-cholinergic effect evidenced by their inactivity against the central or peripheric effects of Oxotremorine.

(2) Cardio vascular effects

In the cardio vascular field in the anesthetized dog, they exert hypertensive and positive inotropic and chronotropic actions of long duration with doses ranging from 0,1 to 1 mg/kg by intravenous way. They seemingly exert not any vaso constricting effect. These actions induce an increase in the cardiac output and the tissular perfusion. In the field of the cardio vascular shock experimentally produced for example by injection of endotoxin or platelet activating factor (PAF), the compounds of this invention at the doses herein above cited and by the same route of administration, antagonize the resulting cardio-vascular failure.

| | | | | | | F °C. | Elementary Analysis (salts) | | | | | |
|---|---|---|---|---|---|---|---|---|---|---|---|---|
| | | | | | | | Theoretical | | | Found | | |
| $R_4$ | $R_3$ | $(Z)_p$ | n | m | p | (sels) | C | H | N | C | H | N |
| H | $C_6H_5$ | H | 0 | 0 | 0 | 174[a] | 62,49 | 5,44 | 10,78 | 62,65 | 5,52 | 10,96 |
| H | 2,6-$Cl_2C_6H_3$ | H | 0 | 0 | 0 | 240[a] | 52,98 | 4,30 | 9,10 | 53,11 | 4,23 | 9,29 |

-continued

| | | | | | | | F °C. | Elementary Analysis (salts) | | | | | |
|---|---|---|---|---|---|---|---|---|---|---|---|---|---|
| | | | | | | | | Theoretical | | | Found | | |
| R$_4$ | R$_3$ | (Z)$_p$ | n | m | p | (sels) | | C | H | N | C | H | N |
| H | 2,6-Cl$_2$C$_6$H$_3$ | H | 1 | 0 | 0 | 145[b] | | 48,36 | 4,61 | 9,43 | 48,43 | 4,74 | 9,41 |
| H | H | H | 1 | 0 | 0 | 100[c] | | 46,30 | 5,66 | 14,50 | 46,17 | 5,64 | 14,68 |
| H | H | 3,4(OCH$_3$)$_2$ | 0 | 0 | 1 | 174[c] | | 43,59 | 5,47 | 12,51 | 43,39 | 5,46 | 12,65 |
| H | 2,6-Cl$_2$C$_6$H$_3$ | 3,4(OCH$_3$)$_2$ | 0 | 0 | 1 | 165[b] | | 46,44 | 4,65 | 8,66 | 46,35 | 4,71 | 8,53 |
| H | H | 4-Cl | 0 | 0 | 1 | 142[c] | | 39,06 | 4,37 | 13,56 | 39,17 | 4,27 | 13,70 |
| H | COOEt | 4-Cl | 0 | 0 | 1 | 191 | | 46,93 | 4,93 | 12,43 | 46,72 | 5,13 | 12,57 |
| H | H | 2,6-Cl$_2$ | 0 | 0 | 2 | 99[c] | | 35,21 | 3,72 | 12,20 | 35,22 | 3,55 | 12,32 |
| H | H | 2-Cl | 0 | 0 | 1 | 132[c] | | 39,14 | 4,38 | 13,88 | 39,176 | 4,27 | 13,71 |
| H | COOEt | H | 1 | 0 | 0 | 121 | | 60,32 | 6,96 | 15,09 | 60,63 | 6,91 | 15,15 |
| H | 2,6-Cl$_2$C$_6$H$_3$ | 4-Cl | 0 | 0 | 1 | 210[b] | | 43,61 | 3,99 | 8,94 | 43,74 | 3,89 | 9,00 |

[c]bromhydrate
[b]sulfonate
[a]fumarate

| Z | P | R | n | X | n$_1$ | m | A | R$_3$ | R$_4$ | P.M. (Base) | MP Brom-hydrate | Theoretical | | | Found | | |
|---|---|---|---|---|---|---|---|---|---|---|---|---|---|---|---|---|---|
| | | | | | | | | | | | | C | H | N | C | H | N |
| 2-CL | 1 | | 0 | O | 1 | 0 | NH | H | H | 239,70 | 135 | 41,21 | 4,72 | 13,11 | 41,21 | 4,83 | 12,62 |
| 2,3-CL 4-MeO | 3 | | 0 | O | 0 | 0 | NH | H | H | 290,15 | 208 | 35,61 | 3,80 | 11,32 | 35,73 | 3,94 | 11,37 |
| 2-CL | 1 | " | " | O | 0 | 0 | NH | H | H (isomere R (+)) | 225,67 | 50 | 39,18 | 4,27 | 13,7 | 38,55 | 4,85 | 10,62 |
| 2-CL | 1 | " | " | O | 0 | 0 | NH | | morpholine | 295,76 | 184[1] | 52,50 | 5,38 | 10,20 | 52,42 | 5,39 | 10,14 |
| 2-CL | 1 | " | " | O | 0 | 0 | NH | | piperidine | 293,79 | 149[1] | 55,68 | 5,90 | 10,25 | 55,53 | 5,78 | 10,18 |
| 3,4-CL | 2 | " | " | O | 0 | 0 | NH | H | H | 260,13 | 178 | 35,2 | 3,54 | 12,32 | 34,99 | 3,76 | 12,30 |
| 2-CL | 1 | " | " | O | 0 | 0 | NH | | piperazine | 294,78 | 168[1] | 50,15 | 5,16 | 10,63 | 50,05 | 5,26 | 10,55 |
| 2-CL 3,4-dimeO | 3 | " | " | O | 0 | 0 | NH | H | H | 285,73 | 120 | 39,31 | 4,67 | 11,46 | 39,52 | 4,81 | 11,62 |
| 2-CL | 1 | " | " | O | 0 | 0 | NH | | 4-(O—methoxyphenyl)-piperazine | 400,90 | 171[1] | 58,08 | 5,65 | 10,84 | 57,95 | 5,74 | 10,77 |
| 2-CL | 1 | " | " | O | 0 | 0 | NH | H | Me | 239,70 | 152[1] | 50,64 | 5,10 | 11,81 | 50,65 | 5,33 | 11,77 |
| 2,4-CL | 2 | " | " | O | 0 | 0 | NH | H | H | 261,13 | 194 | 35,22 | 3,54 | 12,32 | 35,48 | 3,68 | 12,24 |
| 2-CL | 2 | " | " | O | 0 | 0 | NH | H | NH$_2$ | 240,69 | 142[2] | 32,59 | 3,83 | 15,20 | 32,69 | 3,99 | 15,30 |
| 4-Br | 2 | " | " | O | 0 | 0 | NH | H | H | 270,13 | 178 | 34,21 | 3,73 | 11,96 | 34,28 | 3,87 | 11,95 |
| 2,5-CL | 2 | " | " | O | 0 | 0 | NH | H | H | 260,13 | 04 | 35,2 | 3,54 | 12,32 | 35,25 | 3,64 | 12,20 |
| H | | " | " | S | 0 | 0 | NH | H | H | 207,29 | 202 | 41,67 | 4,90 | 14,58 | 41,70 | 4,94 | 14,57 |
| 2-CL | 1 | " | " | O | 0 | 0 | NH | | 4-(pyrimidino-2)-piperazine | 372,85 | 208[1] | 54,05 | 5,15 | 17,19 | 53,88 | 5,16 | 17,05 |
| 2-CL | 1 | " | " | O | 0 | 0 | NH | C$_2$H$_5$ | C$_2$H$_5$ | 281,78 | 173[1] | 54,34 | 6,08 | 10,56 | 54,24 | 6,03 | 10,55 |
| 2-(cyclo-hexene 2) | 1 | " | " | O | 0 | 0 | NH | H | H | 271,36 | 196[1] | 62,00 | 6,50 | 10,84 | 61,84 | 6,66 | 10,84 |
| 2-cyclohexane | 1 | " | " | O | 0 | 0 | NH | H | H | 273,38 | 149 | 54,24 | 6,83 | 11,86 | 54,08 | 6,76 | 11,82 |
| 4-SCH$_3$ | 1 | " | " | O | 0 | 0 | NH | H | H | 237,32 | 157 | 41,52 | 5,07 | 13,20 | 41,75 | 5,11 | 13,01 |
| 2-CL | 1 | " | " | O | 0 | 0 | NH | H | (3,4-dimethoxy-phenyl)-ethane | 375,85 | <50[1] | 56,16 | 5,33 | 8,54 | 53,99 | 5,67 | 8,52 |
| 2-CL | 1 | " | " | O | 0 | 0 | NH | H | (4-hydroxyphenyl)-2-methyl-1-ethane | 359,85 | <50[1] | 58,05 | 5,51 | 8,83 | 55,32 | 5,65 | 8,64 |
| 2-CL | 1 | " | " | O | 0 | 0 | NH | H | H [isomere S (−)] | 225,67 | <50[1] | 39,17 | 4,27 | 13,7 | 39,16 | 4,37 | 13,58 |

What we claim is:
1. A compound selected from the group consisting of compounds of formula I

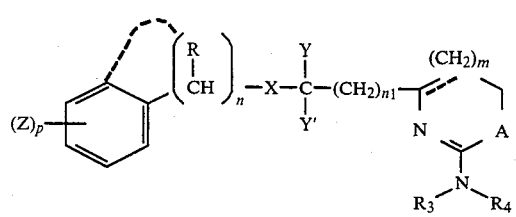

(I)

wherein

Z is hydrogen, a halogen, a lower alkyl radical, a lower alkoxy radical, a trifluoromethyl, a trifluoromethoxy, a cyano group, a nitro group, a carboxamido group, a lower alkenyl radical, a lower alkylthio, a lower alkylene dioxy, a lower cyclo alkenyl radical or a lower cycloalkyl radical;

X is an oxygen, a sulphur atom, a methylene group, a carbon-carbon single bond or an imino group of the formula N-R$_1$ wherein R$_1$ is a hydrogen, a lower alkyl radical, or an acyl residue derived from an organic carboxylic or sulphonic acid;

Y is a hydrogen, a lower alkyl radical, a phenyl radical, a hydroxy or a phenoxy radical or a phenyl radical substituted by from one to three substituents selected from the group consisting of a halogen, a trifluoromethyl, a lower alkyl radical and a lower alkoxy radical;

Y' is a hydrogen;

or Y and Y' together are an oxygen;

or Y forms with the terminal phenyl ring carrying the Z moiety, when n is zero, a bicyclic-homo- or heterocyclic, saturated or unsaturated structure selected from group consisting of benzodioxan, tetrahydroquinoline, tetrahydronaphthalene, dihydronaphthalene, naphthalene-1, naphthalene-2 and benzimidazol;

A is a NH group;

R₃ and R₄ are the same or different, and are hydrogen, a lower alkyl radical, a lower alkenyl radical, an aryl lower alkyl radical wherein the aryl moiety is selected from the group consisting of benzyl, phenethyl, alphamethylphenethyl, 2,6-dichlorobenzyl and 2,3,5-trimethoxybenzyl, a heteroaryl lower alkyl radical wherein the heteroaryl moiety is selected from the group consisting of pyridyl, furyl, pyranyl, and thienyl, a phenyl radical, an alkoxy carbonyl group, an acyl residue from an organic carboxylic acid having from 1 to 10 carbon atoms or an amino group or when R₃ and R₄ are taken together form, with the nitrogen atom to which they are bound, a nitrogen containing ring selected from the group consisting of azetidinyl, pyrrolidinyl, piperidinyl, and hexamethyleneimino;

or where R₃ and R₄ together with said nitrogen form a heterocyclic ring selected from the group consisting of tetrahydropyrimidyl, tetrahydrooxazinyl, morpholyl, thiazinyl, pyrazolidinyl and piperazinyl;

R is a hydrogen, a lower alkyl radical, a phenyl radical substituted by substituents as defined by (Z)p or a phenylene radical linked to the adjacent, terminal (Z)p-substituted phenyl ring by an alkylene chain having 1 or 2 carbon atoms;

n is zero or 1;

n₁ is zero; 1 or 2 m is zero;

p is 1, 2 or 3;

and the combined full and dotted lines signify a bond selected from the group consisting of a carbon-carbon single bond and a carbon-carbon double bond and the pharmaceutically acceptable acid addition salts thereof.

2. A compound according to claim 1 having the formula I$_A$

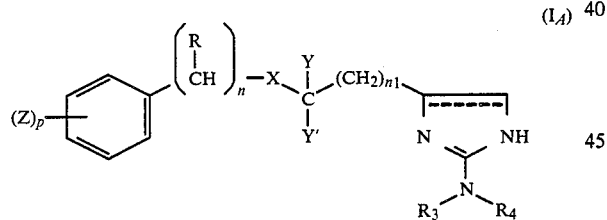

wherein the substituents Z, R, X, Y, Y', R, R₃, R₄, p, n and n₁ are as defined in claim 1.

3. A method for alleviating the acute or chronic cardio-vascular failure which consists in administering to humans suffering from cardio vascular failure and shock condition a safe but effective amount of a compound of claim (1).

4. A method for treating the depressive conditions from endogenous or behavourial origin which consists in administering to depressive human patients a safe but effective amount of a compound of claim (1).

5. A compound of claim 1 wherein

A, R₃, R₄ Y, Y', Z, m, n₁ and p are as defined in claim 1;

n is zero; and

X is selected from the group consisting of oxygen, sulphur, methylene, a carbon-carbon single bond, and imino of the formula >NR₁ wherein R₁ is hydrogen or lower alkyl.

6. A compound of claim 1 wherein A, R₃, R₄, X, Y, Y', Z, m, n₁ and p are as defined in claim 1 R is phenyl substituted by (Z)p and n is 1.

7. A compound according to claim 1 having the formula I''''

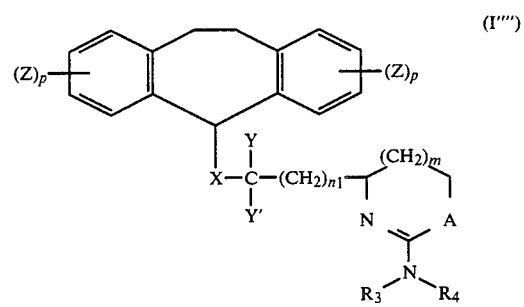

wherein Z, X, Y, Y', R₃, R₄, A, m, n₁ and p are as in claim 1.

8. The method of claim 3 wherein the effective daily dosage in man is between 5 and 1,000 mg.

9. The method of claim 4 wherein the effective daily dosage in man is between 5 and 1,000 mg.

10. A pharmaceutical composition for treating cardiovascular failure or depressive conditions comprising as active ingredient thereof at least one compound of formula I of claim 1 in an amount sufficient to treat the aforesaid conditions, in conjunction with an inert non-toxic pharmaceutically acceptable carrier.

11. A pharmaceutical composition according to claim 10 wherein the carrier or vehicle is one of those suitable for the parenteral, oral, rectal, sublingual, percutaneous or permucous ways of administration.

12. A pharmaceutical composition according to claim 10 wherein the amount of active ingredient ranges from 1 to 500 mg per unit dosage.

* * * * *